United States Patent
Almario-Garcia et al.

(10) Patent No.: US 7,476,756 B2
(45) Date of Patent: Jan. 13, 2009

(54) ALKYL-, ALKENYL- AND ALKYNYLCARBAMATE DERIVATIVES, THEIR PREPARATION AND THEIR APPLICATION IN THERAPEUTICS

(75) Inventors: Antonio Almario-Garcia, Chatenay-Malabry (FR); Pascal George, Longvilliers (FR); Christian Hoornaert, Antony (FR); Adrien Tak Li, Fontenay aux Roses (FR); Frederic Puech, Gif sur Yvette (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/874,959

(22) Filed: Oct. 19, 2007

(65) Prior Publication Data

US 2008/0103197 A1     May 1, 2008

Related U.S. Application Data

(63) Continuation of application No. PCT/FR2006/000958, filed on Apr. 28, 2006.

(30) Foreign Application Priority Data

May 3, 2005    (FR)  .................... 05 04492

(51) Int. Cl.
    *C07C 269/04*     (2006.01)
    *C07C 271/08*     (2006.01)
    *A61K 31/27*     (2006.01)

(52) U.S. Cl. ...................................... 560/157; 514/478

(58) Field of Classification Search ................ 560/157; 514/478

See application file for complete search history.

(56) References Cited

U.S. PATENT DOCUMENTS 5,411,987 A * 5/1995 Wollweber et al. .......... 514/529
5,639,890 A * 6/1997 Henkelmann et al. ....... 548/231

FOREIGN PATENT DOCUMENTS

FR    2843964    3/2004
FR    2854633    11/2004
FR    2860514    4/2005

OTHER PUBLICATIONS

Tarzia, G., et. al., Design, Synthesis, and Structure-Activity Relationships of Alkylcarbamic Acid Aryl Esters, A New Class of Fatty Acid Amide Hydrolase Inhibitors, J. Med. Chem. 2003 vol. 46, pp. 2352-2360.

* cited by examiner

*Primary Examiner*—Shailendra Kumar
(74) *Attorney, Agent, or Firm*—Balaram Gupta

(57) ABSTRACT

The invention relates to a compound of formula (I):

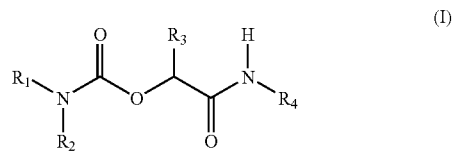

Wherein $R_1$, $R_2$, $R_3$ and $R_4$ are as defined herein. The invention also relates to methods of preparation of compounds of formula (I) as well as to their therapeutic application.

13 Claims, No Drawings

ALKYL-, ALKENYL- AND ALKYNYLCARBAMATE DERIVATIVES, THEIR PREPARATION AND THEIR APPLICATION IN THERAPEUTICS

This application is a continuation of International application No. PCT/FR2006/000,958, filed Apr. 28, 2006, which is incorporated herein by reference in its entirety; which claims the benefit of priority of French Patent Application No. 05/04,492, filed May 3, 2005.

The invention relates to alkyl-, alkenyl- and alkynylcarbamate derivatives, to their preparation and to their application in therapeutics.

The compounds of the invention correspond to the general formula (I)

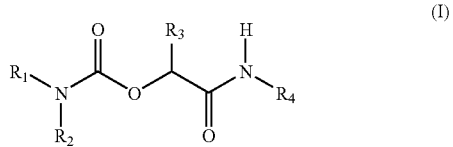

in which $R_1$ represents a $C_{5-26}$-alkyl, $C_{5-26}$-alkenyl or $C_{5-26}$-alkynyl group or a polyunsaturated aliphatic carbon group comprising between 5 and 26 carbon atoms and comprising at least two unsaturations chosen from double and triple bonds;

$R_2$ represents a hydrogen atom or a $C_{1-6}$-alkyl group;

$R_3$ represents a hydrogen atom or a $C_{1-3}$-alkyl;

$R_4$ represents a hydrogen atom or a $C_{1-4}$-alkyl, $C_{3-7}$-cycloalkyl or $C_{3-7}$-cycloalkyl-$C_{1-3}$-alkyl group.

The compounds of general formula (I) can comprise one or more asymmetric carbons. They can exist in the form of enantiomers or of diastereoisomers. The compounds of general formula (I) can also exist in the form of cis or trans stereoisomers. These enantiomers, diastereoisomers and stereoisomers, and their mixtures, including racemic mixtures, form part of the invention.

The compounds of general formula (I) can exist in the form of hydrates or of solvates, namely in the form of combinations or associations with one or more molecules of water or with a solvent. Such hydrates and solvates also form part of the invention.

In the context of the present invention:

$C_{t-z}$ where t and z can take the values from 1 to 26 is understood to mean a carbon chain which can have from t to z carbon atoms, for example $C_{1-3}$ a carbon chain which can have from 1 to 3 carbon atoms;

an alkyl group is understood to mean: a saturated, linear, branched or cyclic aliphatic group; for example a $C_{1-3}$-alkyl group represents a carbon chain which can have from 1 to 3 carbon atoms, for example a methyl, ethyl, propyl, isopropyl, cyclopropyl, and the like;

an alkenyl group is understood to mean: a linear, branched or cyclic alkyl group comprising a double bond, for example a $C_{5-26}$-alkenyl group represents a linear, branched or cyclic carbon chain of 5 to 26 carbon atoms comprising a double bond, for example a pentenyl, cyclopentenyl, hexenyl, cyclohexenyl, heptenyl, cycloheptenyl, octenyl, cyclooctenyl, and the like;

an alkynyl group is understood to mean: a linear, branched or cyclic alkyl group comprising a triple bond, for example a $C_{5-26}$-alkynyl group represents a linear, branched or cyclic carbon chain of 5 to 26 carbon atoms comprising a triple bond, for example a hexynyl, heptynyl, octynyl, and the like;

a polyunsaturated aliphatic carbon group is understood to mean: a linear, branched or cyclic alkyl group comprising at least two unsaturations chosen from double and triple bonds, for example a pentadienyl, hexadienyl, cyclohexadienyl, heptadienyl, heptatrienyl, cycloheptadienyl, cycloheptatrienyl, pentadiynyl, hexadiynyl or heptadiynyl.

Among the compounds of general formula (I) which are subject-matters of the invention, a first group of compounds is composed of the compounds for which:

$R_1$ represents
a $C_{5-26}$-alkyl group, more particularly a pentyl, hexyl, heptyl, octyl, cyclooctyl, 1-methylheptyl, nonyl, decyl, 1-methyldecyl, dodecyl, cyclododecyl, tetradecyl, 1-methyltridecyl, pentadecyl, octadecyl or nonadecyl;
a $C_{5-26}$-alkenyl group, more particularly a hexenyl, octenyl, tetradecenyl, hexadecenyl, octadecenyl or icosenyl group;
or a polyunsaturated aliphatic carbon group comprising between 5 and 26 carbon atoms and comprising at least two unsaturations chosen from double bonds, more particularly an octadecatrienyl, nonadecatetraenyl, icosadienyl, icosatrienyl or icosatetraenyl;

and/or $R_2$ represents a hydrogen atom or a $C_{1-6}$-alkyl group, more particularly a methyl or a hexyl;

and/or $R_3$ represents a hydrogen atom or a $C_{1-3}$-alkyl group;

and/or $R_4$ represents a hydrogen atom or a $C_{1-4}$-alkyl, $C_{3-7}$-cycloalkyl or $C_{3-7}$-cycloalkyl-$C_{1-3}$-alkyl group.

Mention may be made, among the compounds of this first group, of the compounds of formula (I) for which:

$R_3$ represents a hydrogen atom or a $C_{1-3}$-alkyl group, more particularly a methyl;

and/or $R_4$ represents a hydrogen atom or a $C_{1-4}$-alkyl group, more particularly a methyl.

Mention may in particular be made, among the compounds of this first group, of the following compounds:

2-Amino-1-methyl-2-oxoethyl (pent-1-yl)carbamate
2-(Methylamino)-2-oxoethyl ((2E)-hex-2-en-1-yl)carbamate
2-Amino-2-oxoethyl ((2E)-hex-2-en-1-yl)carbamate
2-Amino-2-oxoethyl ((2Z)-hex-2-en-1-yl)carbamate
2-Amino-2-oxoethyl ((3Z)-hex-3-en-1-yl)carbamate
2-Amino-2-oxoethyl ((3E)-hex-3-en-1-yl)carbamate
2-(Methylamino)-2-oxoethyl ((3Z)-hex-3-en-1-yl)carbamate
2-(Methylamino)-2-oxoethyl ((3E)-hex-3-en-1-yl)carbamate
2-(Methylamino)-2-oxoethyl ((2Z)-hex-2-en-1-yl)carbamate
2-(Methylamino)-2-oxoethyl (hex-1-yl)carbamate
2-Amino-1-methyl-2-oxoethyl (hex-1-yl)carbamate
2-(Methylamino)-2-oxoethyl (dihex-1-yl)carbamate
2-(Methylamino)-2-oxoethyl (hept-1-yl)carbamate
2-(Methylamino)-2-oxoethyl ((2E)-oct-2-en-1-yl)carbamate
2-Amino-2-oxoethyl ((2E)-oct-2-en-1-yl)carbamate
2-(Methylamino)-2-oxoethyl ((3Z)-oct-3-en-1-yl)carbamate
2-Amino-2-oxoethyl ((3Z)-oct-3-en-1-yl)carbamate
2-Amino-2-oxoethyl ((5Z)-oct-5-en-1-yl)carbamate
2-(Methylamino)-2-oxoethyl ((5Z)-oct-5-en-1-yl)carbamate
2-Amino-2-oxoethyl (oct-7-en-1-yl)carbamate 2-(Methylamino)-2-oxoethyl (oct-7-en-1-yl)carbamate
2-(Methylamino)-2-oxoethyl (cyclooct-1-yl)carbamate
2-Amino-1-methyl-2-oxoethyl (oct-1-yl)carbamate
2-(Methylamino)-2-oxoethyl (1-methylhept-1-yl)carbamate
2-(Methylamino)-2-oxoethyl (non-1-yl)carbamate
2-(Methylamino)-2-oxoethyl (dec-1-yl)carbamate
2-Amino-1-methyl-2-oxoethyl (dec-1-yl)carbamate
2-(Methylamino)-2-oxoethyl (1-methyldec-1-yl)carbamate
2-(Methylamino)-2-oxoethyl (cyclododec-1-yl)carbamate
2-(Methylamino)-2-oxoethyl (dodec-1-yl)carbamate
2-Amino-2-oxoethyl ((11Z)-tetradec-11-en-1-yl)carbamate
2-(Methylamino)-2-oxoethyl ((11Z)-tetradec-11-en-1-yl) carbamate
2-(Methylamino)-2-oxoethyl (tetradec-1-yl)carbamate
2-Amino-2-oxoethyl ((9Z)-hexadec-9-en-1-yl)carbamate
2-(Methylamino)-2-oxoethyl ((9Z)-hexadec-9-en-1-yl) carbamate
2-(Methylamino)-2-oxoethyl (1-methyltridecyl)carbamate
2-(Methylamino)-2-oxoethyl (pentadec-1-yl)carbamate
2-(Methylamino)-2-oxoethyl ((6E,9E,12E)-octadeca-6,9,12-trien-1-yl)carbamate
2-Amino-2-oxoethyl ((6Z)-octadec-6-en-1-yl)carbamate
2-(Methylamino)-2-oxoethyl ((6Z)-octadec-6-en-1-yl) carbamate
2-(Methylamino)-2-oxoethyl ((methyl)octadec-1-yl)carbamate
2-Amino-2-oxoethyl ((4Z,7Z,10Z,13Z)-nonadeca-4,7,10,13-tetraen-1-yl)carbamate
2-(Methylamino)-2-oxoethyl (nonadec-1-yl)carbamate
2-(Methylamino)-2-oxoethyl ((5Z,8Z,11Z,14Z)-icosa-5,8,11,14-tetraen-1-yl)carbamate
2-(Methylamino)-2-oxoethyl ((11E,14E,17E)-icosa-11,14,17-trien-1-yl)carbamate
2-(Methylamino)-2-oxoethyl ((11E,14E)-icosa-11,14-dien-1-yl)carbamate
2-(Methylamino)-2-oxoethyl ((11E)-icosa-11-en-1-yl) carbamate.

Among the compounds of general formula (I) which are subject-matters of the invention, a second group of compounds is composed of the compounds for which:

$R_1$ represents a $C_{10-20}$-alkyl, $C_{10-20}$-alkenyl or $C_{10-20}$-alkynyl group or a polyunsaturated aliphatic carbon group comprising between 10 and 20 carbon atoms and comprising at least two unsaturations chosen from double and triple bonds;

and/or $R_2$ represents a hydrogen atom or a $C_{1-6}$-alkyl group, more particularly a methyl or a hexyl;

and/or $R_3$ represents a hydrogen atom or a $C_{1-3}$-alkyl group;

and/or $R_4$ represents a hydrogen atom or a $C_{1-4}$-alkyl, $C_{3-7}$-cycloalkyl or $C_{3-7}$-cycloalkyl-$C_{1-3}$-alkyl group.

Mention may be made, among the compounds of this second group, of the compounds of formula (I) for which:

$R_1$ represents a $C_{10-20}$-alkyl group, more particularly a decyl, methyldecyl, dodecyl, cyclododecyl, methyltridecyl, tetradecyl, pentadecyl, octadecyl or nonadecyl, a $C_{10-20}$-alkenyl group, more particularly a tetradecenyl, hexadecenyl, octadecenyl or icosenyl, or a polyunsaturated aliphatic carbon group comprising between 10 and 20 carbon atoms and comprising at least two unsaturations chosen from double bonds, more particularly an octadecatrienyl, nonadecatetraenyl, icosadienyl, icosatrienyl or icosatetraenyl;

and/or $R_2$ represents a hydrogen atom or a $C_{1-6}$-alkyl group, more particularly a methyl;

and/or $R_3$ represents a hydrogen atom or a $C_{1-3}$-alkyl group, more particularly a methyl;

and/or $R_4$ represents a hydrogen atom or a $C_{1-4}$-alkyl group, more particularly a methyl.

The following compounds may be mentioned among the compounds of the subgroup defined above:

2-(Methylamino)-2-oxoethyl (dec-1-yl)carbamate
2-(Methylamino)-2-oxoethyl (1-methyldec-1-yl)carbamate
2-(Methylamino)-2-oxoethyl (cyclododec-1-yl)carbamate
2-(Methylamino)-2-oxoethyl (dodec-1-yl)carbamate
2-Amino-2-oxoethyl ((11Z)-tetradec-11-en-1-yl)carbamate
2-(Methylamino)-2-oxoethyl ((11Z)-tetradec-11-en-1-yl) carbamate
2-(Methylamino)-2-oxoethyl (tetradec-1-yl)carbamate
2-Amino-2-oxoethyl ((9Z)-hexadec-9-en-1-yl)carbamate
2-(Methylamino)-2-oxoethyl ((9Z)-hexadec-9-en-1-yl) carbamate
2-(Methylamino)-2-oxoethyl (1-methyltridecyl)carbamate
2-(Methylamino)-2-oxoethyl (pentadec-1-yl)carbamate
2-(Methylamino)-2-oxoethyl ((6E,9E,12E)-octadeca-6,9,12-trien-1-yl)carbamate
2-(Methylamino)-2-oxoethyl ((6Z)-octadec-6-en-1-yl) carbamate
2-(Methylamino)-2-oxoethyl ((5Z,8Z,11Z,14Z)-icosa-5,8,11,14-tetraen-1-yl)carbamate
2-(Methylamino)-2-oxoethyl ((11E,14E,17E)-icosa-11,14,17-trien-1-yl)carbamate
2-(Methylamino)-2-oxoethyl ((11E,14E)-icosa-11,14-dien-1-yl)carbamate.

The compounds of the invention can be prepared according to various methods illustrated by the schemes which follow.

Thus, according to a first method (Scheme 1), the compounds of general formula (I) can be prepared by reacting an amine of general formula (II), in which $R_1$ and $R_2$ are as defined in the general formula (I), with a carbonate of general formula (III), in which Z represents a hydrogen atom or a nitro group while $R_3$ and $R_4$ are as defined in the general formula (I).

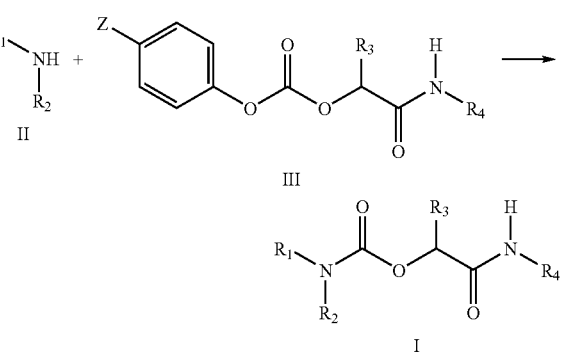

The carbonates of general formula (III) can be prepared according to any method described in the literature, for example by reaction of an alcohol of general formula $HOCHR_3CONHR_4$, where $R_3$ and $R_4$ are as defined in the general formula (I), with phenyl or 4-nitrophenyl chloroformate in the presence of a base, such as triethylamine or diisopropylethylamine.

Another method (Scheme 2) for obtaining compounds of general formula (I) in which $R_2$ represents a hydrogen atom consists in reacting a compound of general formula (IV), in which $R_1$ is as defined in the general formula (I) and W represents a hydroxyl, mesylate or tosylate group or a chlorine, bromine or iodine atom, with an oxazolidinedione of general structure (V), in which $R_3$ is as defined in the general formula (I), in order to provide the oxazolidinedione derivative of general structure (VI).

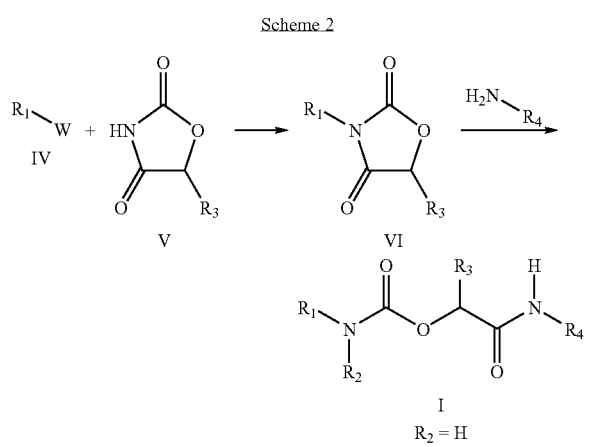

Scheme 2

In the case where W represents a hydroxyl group, the reaction can be carried out according to the Mitsunobu conditions (Synthesis, 1981, 1-28), for example by the action of diethyl or diisopropyl azodicarboxylate in the presence of triphenylphosphine. In the case where W represents a chlorine, bromine or iodine atom or a mesylate or tosylate group, the reaction can be carried out in the presence of a base, such as 1,1,3,3-tetramethylguanidine, sodium hydride or sodium tert-butoxide, in a solvent, such as tetrahydrofuran, acetonitrile or dimethylformamide, at a temperature between 0° C. and 80° C. The oxazolidinedione derivative of general formula (VI) thus obtained is subsequently converted to the compound of general formula (I) in which $R_2$ represents a hydrogen atom by aminolysis using an amine of general formula $R_4NH_2$ where $R_4$ is as defined in the general formula (I).

The compounds of general formulae (II), (IV) and (V) and also the alcohols of general formula $HOCHR_3CONHR_4$ and the amines of general formula $R_4NH_2$, when their method of preparation is not described, are available commercially or are described in the literature or can be prepared according to various methods described in the literature or known to a person skilled in the art.

The invention, according to another aspect of its aspects, also has as subject-matter the compounds of formula (VI). These compounds are of use as intermediates in the synthesis of the compounds of formula (I).

The examples which follow illustrate the preparation of some compounds of the invention. These examples are not limiting and serve only to illustrate the invention. The microanalyses, the IR and NMR spectra and/or LC-MS (liquid chromatography coupled to mass spectroscopy) confirm the structures and the purities of the compounds obtained.

M.p. (° C.) represents the melting point in degrees Celsius. The numbers shown between brackets in the titles of the examples correspond to those in the 1st column of the table below.

EXAMPLE 1

2-(Methylamino)-2-oxoethyl decylcarbamate (compound No. °26)

A solution of 136 mg (0.65 mmol) of 2-(methylamino)-2-oxoethyl phenyl carbonate and of 133 mg (0.85 mmol) of decylamine in 2 ml of dichloromethane is stirred at ambient temperature for 18 h.

The solvent is evaporated under reduced pressure and the evaporation residue is chromatographed on a column of silica gel, elution being carried out with a 2% mixture of methanol in dichloromethane.

The product obtained is crystallized from diisopropyl ether to result in 135 mg of white solid.

LC-MS: M+H=273

M.p. (° C.): 98-100° C.

$^1$H NMR (CDCl$_3$) • (ppm): 6.10 (broad signal, 1H), 4.80 (broad signal, 1H), 4.60 (s, 2H), 3.20 (q, 2H), 2.85 (d, 3H), 1.65-1.45 (m, 4H), 1.45-1.20 (m, 2H), 1.00-0.80 (m, 3H).

EXAMPLE 2

2-(Methylamino)-2-oxoethyl ((11Z)-tetradec-11-en-1-yl)carbamate (compound No. 32)

2.1 3-[(11Z)-tetradec-11-en-1-yl]-1,3-oxazolidine-2,4-dione 420 mg (1.98 mmol) of (11Z)-tetradec-11-en-1-ol, in solution in 2 ml of tetrahydrofuran, are added to a solution of 200 mg (1.98 mmol) of 1,3-oxazolidine-2,4-dione and of 571 mg (2.18 mmol) of triphenylphosphine in 4 ml of tetrahydrofuran. 0.99 ml (2.2 mmol) of a 40% solution of diethyl azodicarboxylate in toluene is subsequently added dropwise. The mixture is stirred at ambient temperature for 5 h.

The solvent is evaporated under reduced pressure and the evaporation residue is purified by chromatography on a column of silica gel, elution being carried out with a gradient of 10 to 50% of ethyl acetate in cyclohexane. 490 mg of a yellow oil are thus obtained.

$^1$H NMR (CDCl$_3$) δ (ppm): 5.25 (m, 2H), 4.60 (s, 2H), 3.45 (t, 2H), 2.10-1.80 (m, 4H), 1.65-1.45 (m, 2H), 1.40-1.05 (m, 14H), 0.90 (t, 3H).

2.2 2-(methylamino)-2-oxoethyl ((11Z)-tetradec-11-en-1-yl)carbamate 6 ml of a 2M solution of methylamine in methanol are added to a solution of 240 mg (0.81 mmol) of 3-[(11Z)-tetradec-11-en-1-yl]-1,3-oxazolidine-2,4-dione, obtained in stage 2.1, in 1.5 ml of methanol.

The mixture is stirred at ambient temperature for 2 h, then the solvent is evaporated under reduced pressure and the evaporation residue is purified by chromatography on a column of silica gel, elution being carried out with a gradient of 70 to 100% of ethyl acetate in cyclohexane.

A yellow solid is isolated and is treated with ultrasound for 30 minutes in a mixture of 0.5 ml of ethyl acetate and of 4 ml of cyclohexane. The solid is separated by centrifuging and removing the supernatant.

After drying, 74 mg of a pale yellow solid are thus obtained.

LC-MS: M+H=327

M.p. (° C.): 79-81° C.

$^1$H NMR (d$_6$-DMSO) δ (ppm): 7.75 (broad s, 1H), 7.15 (broad t, 1H), 5.30 (m, 2H), 4.30 (s, 2H), 2.95 (m, 2H), 1.60 (d, 3H), 1.95 (m, 4H), 1.40-1.15 (m, 16H), 0.90 (t, 3H).

EXAMPLE 3

2-amino-2-oxoethyl ((11Z)-tetradec-11-en-1-yl)carbamate (compound No. 31)

6 ml of a 2M solution of ammonia in methanol are added to a solution of 240 mg (0.81 mmol) of 3-[(11Z)-tetradec-11-en-1-yl]-1,3-oxazolidine-2,4-dione, obtained in stage 2.1 of Example 2, in 1.5 ml of methanol.

The mixture is stirred at ambient temperature for 18 h and then the solvent is evaporated under reduced pressure. The evaporation residue is chromatographed on a column of silica gel, elution being carried out with a gradient of 80 to 100% of ethyl acetate in cyclohexane.

A yellow solid is isolated and is treated with ultrasound for 30 minutes in a mixture of 1 ml of ethyl acetate and of 4 ml of cyclohexane. The solid is separated by centrifuging and removing the supernatant.

After drying, 99 mg of a pale yellow solid are thus obtained.

LC-MS: M+Na=335

M.p. (° C.): 120-123° C.

$^1$H NMR (d$_6$-DMSO) δ (ppm): 7.30-7.05 (m, 3H), 5.30 (m, 2H), 4.30 (s, 2H), 2.95 (m, 2H), 2.00 (m, 4H), 1.45-1.15 (m, 16H), 0.90 (t, 3H).

The chemical structures and the physical properties of some compounds according to the invention are illustrated in the following Table 1.

In this table:
- the "M.p. (° C.)" column teaches the melting points of the products in degrees Celsius. "N.D" means that the melting point is not determined.
- the "LC-MS or (MS)" column teaches the results of analysis of products by LC-MS (liquid chromatography coupled to mass spectroscopy), carried out on an Agilent LC-MSD Trap device in positive ESI mode, or by MS (mass spectroscopy), on an Autospec M device (EBE) using the DCI-NH$_3$ technique.

TABLE 1

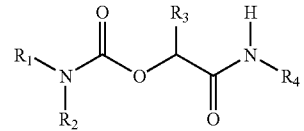

(I)

| No. | R$_1$ | R$_2$ | R$_3$ | R$_4$ | M.p. (° C.) | LC-MS or (MS) |
|---|---|---|---|---|---|---|
| 1 | Pent-1-yl | H | CH3 | H | 132-134 | (M + H 203) |
| 2 | (2E)-Hex-2-en-1-yl | H | H | CH3 | 85-87 | M + Na 237 |
| 3 | (2E)-Hex-2-en-1-yl | H | H | H | 126-128 | M + Na 223 |
| 4 | (2Z)-Hex-2-en-1-yl | H | H | H | 102-104 | M + Na 223 |
| 5 | (3Z)-Hex-3-en-1-yl | H | H | H | N.D | M + Na 223 |
| 6 | (3E)-Hex-3-en-1-yl | H | H | H | 138-140 | M + Na 223 |
| 7 | (3Z)-Hex-3-en-1-yl | H | H | CH3 | 72-74 | M + Na 237 |
| 8 | (3E)-Hex-3-en-1-yl | H | H | CH3 | 88-90 | M + Na 237 |
| 9 | (2Z)-Hex-2-en-1-yl | H | H | CH3 | 74-76 | M + Na 237 |
| 10 | Hex-1-yl | H | H | CH3 | 86-88 | M + H 217 |
| 11 | Hex-1-yl | H | CH3 | H | 123-125 | (M + H 217) |
| 12 | Hex-1-yl | Hex-1-yl | H | CH3 | N.D | M + H 301 |
| 13 | Hept-1-yl | H | H | CH3 | 87-89 | M + H 231 |
| 14 | (2E)-Oct-2-en-1-yl | H | H | CH3 | 80-82 | M + Na 265 |
| 15 | (2E)-Oct-2-en-1-yl | H | H | H | 126-128 | M + Na 251 |
| 16 | (3Z)-Oct-3-en-1-yl | H | H | CH3 | 62-64 | M + Na 265 |
| 17 | (3Z)-Oct-3-en-1-yl | H | H | H | 113-115 | M + Na 251 |
| 18 | (5Z)-Oct-5-en-1-yl | H | H | H | 122-124 | M + Na 251 |
| 19 | (5Z)-Oct-5-en-1-yl | H | H | CH3 | 69-71 | M + Na 265 |
| 20 | Oct-7-en-1-yl | H | H | H | 122-124 | M + Na 251 |
| 21 | Oct-7-en-1-yl | H | H | CH3 | 72-74 | M + Na 265 |
| 22 | Cyclooct-1-yl | H | H | CH3 | 81-83 | M + H 243 |
| 23 | Oct-1-yl | H | CH3 | H | 130-132 | (M + H 245) |

TABLE 1-continued (I)

| No. | R$_1$ | R$_2$ | R$_3$ | R$_4$ | M.p. (°C.) | LC-MS or (MS) |
|---|---|---|---|---|---|---|
| 24 | 1-Methylhept-1-yl | H | H | CH3 | N.D | M + H 267 |
| 25 | Non-1-yl | H | H | CH3 | 95-97 | M + H 259 |
| 26 | Dec-1-yl | H | H | CH3 | 98-100 | M + H 273 |
| 27 | Dec-1-yl | H | CH3 | H | 133-135 | (M + H 273) |
| 28 | 1-Methyldec-1-yl | H | H | CH3 | 71-73 | M + H 287 |
| 29 | Cyclododec-1-yl | H | H | CH3 | 171-173 | M + H 299 |
| 30 | Dodec-1-yl | H | H | CH3 | 103-105 | M + H 301 |
| 31 | (11Z)-Tetradec-11-en-1-yl | H | H | H | 120-123 | M + Na 335 |
| 32 | (11Z)-Tetradec-11-en-1-yl | H | H | CH3 | 79-81 | M + H 327 |
| 33 | Tetradec-1-yl | H | H | CH3 | 106-108 | M + H 329 |
| 34 | (9Z)-Hexadec-9-en-1-yl | H | H | H | 127-129 | M + H 341<br>M + Na 363 |
| 35 | (9Z)-Hexadec-9-en-1-yl | H | H | CH3 | 69-71 | M + H 355<br>M + Na 377 |
| 36 | 1-Methyltridecyl | H | H | CH3 | 82-84 | M + H 329 |
| 37 | Pentadec-1-yl | H | H | CH3 | 107-109 | M + H 343 |
| 38 | (6E, 9E, 12E)-Octadeca-6,9,12-trien-1-yl | H | H | CH3 | N.D | M + H 379 |
| 39 | (6Z)-Octadec-6-en-1-yl | H | H | H | 100-102 | M + H 369<br>M + Na 391 |
| 40 | (6Z)-Octadec-6-en-1-yl | H | H | CH3 | 72-74 | M + H 383 |
| 41 | Octadec-1-yl | CH3 | H | CH3 | 85-87 | M + H 399 |
| 42 | (4Z, 7Z, 10Z, 13Z)-Nonadeca-4,7,10,13-tetraen-1-yl | H | H | H | N.D | M + H 377 |
| 43 | Nonadec-1-yl | H | H | CH3 | 113-115 | M + H 399 |
| 44 | (5Z, 8Z, 11Z, 14Z)-Icosa-5,8,11,14-tetraen-1-yl | H | H | CH3 | N.D | M + H 405 |
| 45 | (11E, 14E, 17E)-Icosa-11,14,17-trien-1-yl | H | H | CH3 | 57-59 | M + H 407<br>M + Na 429 |
| 46 | (11E, 14E)-Icosa-11,14-dien-1-yl | H | H | CH3 | 58-60 | M + H 409<br>M + Na 431 |
| 47 | (11E)-Icosa-11-en-1-yl | H | H | CH3 | 77-79 | M + H 411<br>M + Na 433 |

The compounds of the invention have formed the subject of pharmacological trials which make it possible to determine their inhibitory effect on the enzyme FAAH (Fatty Acid Amido Hydrolase).

The inhibitory activity was demonstrated in a radioenzymatic test based on the measurement of the product of hydrolysis ((1-$^3$H)ethanolamine) of ((1-$^3$H)ethanolamine)-anandamide by FAAH (*Life Sciences* (1995), 56, 1999-2005 and *Journal of Pharmacology and Experimental Therapeutics* (1997), 283, 729-734). Thus, mouse brains (minus the cerebellum) are removed and stored at −80° C. The membrane homogenates are prepared at the time of use by homogenization of the tissues with a Polytron in a 10 mM Tris-HCl buffer (pH 8) comprising 150 mM NaCl and 1 mM EDTA. The enzymatic reaction is subsequently carried out in 70 µl of buffer comprising bovine serum albumin free from fatty acids (1 mg/ml). The test compounds, at various concentrations, the ((1-$^3$H)ethanolamine)-anandamide (specific activity of 15-20 Ci/mmol), diluted to 10 µM with non-radiolabelled anandamide, and the membrane preparation (400 µg of frozen tissue per assay) are successively added. After 15 minutes at 25° C., the enzymatic reaction is halted by addition of 140 µl of chloroform/methanol (2:1). The mixture is stirred for 10 minutes and is then centrifuged at 3500 g for 15 minutes. An aliquot (30 µl) of the aqueous phase comprising the (1-$^3$H) ethanolamine is counted by liquid scintillation.

Under these conditions, the most active compounds of the invention exhibit IC$_{50}$ values (concentration which inhibits the control enzymatic activity of FAAH by 50%) of between 0.001 and 1 µM.

For example, compounds Nos. 13, 22, 24 and 47 in the table respectively exhibit IC$_{50}$ values of 0.091, 0.696, 0.089 and 0.154 µM respectively.

It is therefore apparent that the compounds according to the invention have an inhibitory activity on the enzyme FAAH.

The in vivo activity of the compounds of the invention was evaluated in a test for analgesia.

Thus, the intraperitoneal (i.p.) administration of PBQ (phenylbenzoquinone, 2 mg/kg in a 0.9% sodium chloride solution comprising 5% of ethanol) to male OF1 mice weighing 25 to 30 g causes abdominal tractions, on average 30 twisting or contracting motions during the period from 5 to 15 minutes after injection. The test compounds are administered, orally (p.o.) or intraperitoneally (i.p.) in suspension in 0.5% Tween 80, 60 minutes or 120 minutes before the administration of PBQ. Under these conditions, the most powerful compounds of the invention reduce by 35 to 70% the number of tractions induced by the PBQ, within a range of doses of between 1 and 30 mg/kg.

The enzyme FAAH (*Chemistry and Physics of Lipids*, (2000), 108, 107-121) catalyses the hydrolysis of endogenous derivatives of amides and esters of various fatty acids, such as N-arachidonoylethanolamine (anandamide), N-palmitoylethanolamine, N-oleoylethanolamine, oleamide or 2-arachidonoylglycerol. These derivatives have various pharmacological activities by interacting, inter alia, with the cannabinoid and vanilloid receptors.

The compounds of the invention block this decomposition pathway and increase the tissue level of these endogenous substances. They can therefore be used in the prevention and treatment of pathologies in which endogenous cannabinoids and/or any other substrate metabolized by the enzyme FAAH are involved.

Mention may be made, for example, of the following diseases and conditions:

pain, in particular acute or chronic pain of neurogenic type: migraine, neuropathic pain, including forms associated with the herpes virus and with diabetes; acute or chronic pain associated with inflammatory diseases: arthritis, rheumatoid arthritis, osteoarthritis, spondylitis, gout, vasculitis, Crohn's disease, irritable bowel syndrome; acute or chronic peripheral pain; dizziness, vomiting, nausea, in particular resulting from chemotherapy; eating disorders, in particular anorexia and cachexia of various natures; neurological and psychiatric pathologies: tremors, dyskinesias, dystonias, spasticity, obsessive-compulsive behavior, Tourette's syndrome, all forms of depression and of anxiety of any nature and origin, mood disorders, psychoses; acute or chronic neurodegenerative diseases: Parkinson's disease, Alzheimer's disease, senile dementia, Huntington's chorea, lesions related to cerebral ischemia and to cranial and medullary trauma; epilepsy; sleep disorders, including sleep apnea; cardiovascular diseases, in particular hypertension, cardiac arrhythmias, arteriosclerosis, heart attack, cardiac ischemia; renal ischemia; cancers: benign skin tumors, brain tumors and papillomas, prostate tumors, cerebral tumors (glioblastomas, medulloepitheliomas, medulloblastomas, neuroblastomas, tumors of embryonic origin, astrocytomas, astroblastomas, ependymomas, oligodendrogliomas, plexus tumor, neuroepitheliomas, epiphyseal tumor, ependymoblastomas, malignant meningiomas, sarcomatosis, malignant melanomas, schwannomas); disorders of the immune system, in particular autoimmune diseases: psoriasis, lupus erythematosus, diseases of the connective tissue or collagen diseases, Sjögren's syndrome, ankylosing spondylitis, undifferentiated spondylitis, Behcet's disease, autoimmune hemolytic anemia, multiple sclerosis, amyotrophic lateral sclerosis, amyloidosis, graft rejection, diseases affecting the plasmocytic line; allergic diseases: immediate or delayed hypersensitivity, allergic rhinitis or conjunctivitis, contact dermatitis; parasitic, viral or bacterial infectious diseases: AIDS, meningitis; inflammatory diseases, in particular joint diseases: arthritis, rheumatoid arthritis, osteoarthritis, spondylitis, gout, vasculitis, Crohn's disease, irritable bowel syndrome; osteoporosis; eye conditions: ocular hypertension, glaucoma; pulmonary conditions: diseases of the respiratory tract, bronchospasm, coughing, asthma, chronic bronchitis, chronic obstruction of the respiratory tract, emphysema; gastrointestinal diseases: irritable bowel syndrome, inflammatory intestinal disorders, ulcers, diarrhea; urinary incontinence and bladder inflammation.

The compounds of the invention can thus be used in the preparation of medicaments, in particular of medicaments which are inhibitors of the enzyme FAAH.

Thus, according to another of its aspects, a subject-matter of the invention is medicaments which comprise a compound of formula (I) or a hydrate or a solvate of the compound of formula (I).

These medicaments are used in therapeutics, in particular in the treatment and the prevention of the above-mentioned pathologies.

According to another of its aspects, the present invention relates to pharmaceutical compositions comprising, as active principle, a compound according to the invention. These pharmaceutical compositions comprise an effective dose of at least one compound according to the invention or a hydrate or a solvate of the said compound and at least one pharmaceutically acceptable excipient.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I) above or its optional solvate or hydrate can be administered in a single-dose administration form, as a mixture with conventional pharmaceutical excipients, to animals and to man for the prophylaxis or the treatment of the above disorders or diseases.

Appropriate single-dose administration forms comprise oral forms, such as tablets, soft or hard gelatin capsules, powders, granules, chewing gums and oral solutions or suspensions, forms for sublingual, buccal, intratracheal, intraocular or intranasal administration or for administration by inhalation, forms for subcutaneous, intramuscular or intravenous administration and forms for rectal or vaginal administration. For topical application, the compounds according to the invention can be used in creams, ointments or lotions.

By way of example, a single-dose administration form of a compound according to the invention in the form of a tablet can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said single-dose forms comprise a dose which makes possible a daily administration of 0.1 to 20 mg of active principle per kg of body weight, depending upon the pharmaceutical dosage form.

There may be specific cases where higher or lower dosages are appropriate; such dosages also come within the invention. According to the usual practice, the dosage appropriate to each patient is determined by the doctor according to the method of administration, the weight and the response of the said patient.

According to another of its aspects, the invention also relates to a method for the treatment of the pathologies indicated above which comprises the administration of an effective dose of a compound according to the invention or of a solvate or of a hydrate of the said compound.

What is claimed is:

1. A compound of the formula (I):

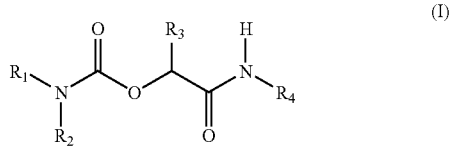

in which
R$^1$ represents a C$_{5-26}$-alkyl, C$_{5-26}$-alkenyl or C$_{5-26}$-alkynyl group or a polyunsaturated aliphatic carbon group comprising between 5 and 26 carbon atoms and comprising at least two unsaturations chosen from double and triple bonds;
R$_2$ represents a hydrogen atom or a C$_{1-6}$-alkyl group;
R$_3$ represents a hydrogen atom or a C$_{1-3}$-alkyl group; and
R$_4$ represents a hydrogen atom or a C$_{1-4}$-alkyl, C$_{3-7}$-cycloalkyl or C$_{3-7}$-cycloalkyl-C$_{1-3}$-alkyl group;
or a hydrate or a solvate thereof.

2. The compound of formula (I) according to claim 1, wherein:
R$_1$ represents a C$_{5-26}$-alkyl group, a C$_{5-26}$-alkenyl group or a polyunsaturated aliphatic carbon group comprising between 5 and 26 carbon atoms and comprising at least two unsaturations chosen from double bonds;
R$_2$ represents a hydrogen atom or a C$_{1-6}$-alkyl group;
R$_3$ represents a hydrogen atom or a C$_{1-3}$-alkyl group; and
R$_4$ represents a hydrogen atom or a C$_{1-4}$-alkyl, C$_{3-7}$-cycloalkyl or C$_{3-7}$-cycloalkyl-C$_{1-3}$-alkyl group;
or a hydrate or a solvate thereof.

3. The compound of formula (I) according to claim 1, wherein:
R$_3$ represents a hydrogen atom or a C$_{1-3}$-alkyl group; and
R$_4$ represents a hydrogen atom or a C$_{1-4}$-alkyl group;
or a hydrate or a solvate thereof.

4. The compound of formula (I) according to claim 2, wherein:
R$_3$ represents a hydrogen atom or a C$_{1-3}$-alkyl group; and
R$_4$ represents a hydrogen atom or a C$_{1-4}$-alkyl group;
or a hydrate or a solvate thereof.

5. The compound of formula (I) according to claim 1, wherein:
R$_1$ represents a C$_{10-20}$-alkyl, C$_{10-20}$-alkenyl or C$_{10-20}$-alkynyl group or a polyunsaturated aliphatic carbon group comprising between 10 and 20 carbon atoms and comprising at least two unsaturations chosen from double and triple bonds;
R$_2$ represents a hydrogen atom or a C$_{1-6}$-alkyl group;
R$_3$ represents a hydrogen atom or a C$_{1-3}$-alkyl group; and
R$_4$ represents a hydrogen atom or a C$_{1-4}$-alkyl, C$_{3-7}$-cycloalkyl or C$_{3-7}$-cycloalkyl-C$_{1-3}$-alkyl group;
or a hydrate or a solvate thereof.

6. The compound of formula (I) according to claim 1, wherein:
R$_1$ represents a C$_{10-20}$-alkyl group, a C$_{10-20}$-alkenyl group or a polyunsaturated aliphatic carbon group comprising between 10 and 20 carbon atoms and comprising at least two unsaturations chosen from double bonds;
R$_2$ represents a hydrogen atom or a C$_{1-6}$-alkyl group;
R$_3$ represents a hydrogen atom or a C$_{1-3}$-alkyl group; and R$_4$ represents a hydrogen atom or a C$_{1-4}$-alkyl group;
or a hydrate or a solvate thereof.

7. A process for the preparation of a compound of formula (I) according to claim 1, comprising:
reacting an amine of formula R$_1$R$_2$NH (II), in which R$_1$ and R$_2$ are as defined in claim 1, with a carbonate of formula (III)

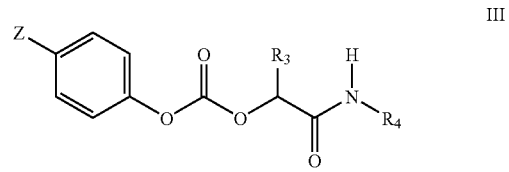

in which Z represents a hydrogen atom or a nitro group and R$_3$ and R$_4$ are as defined in claim 1.

8. A process for the preparation of a compound of formula (I) according to claim 1 and in which R$_2$ represents a hydrogen atom, comprising:
converting the oxazolidinedione derivative of formula (VI)

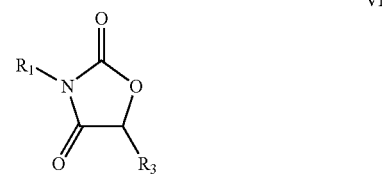

in which R$_1$ and R$_3$ are as defined in claim 1, by aminolysis using an amine of formula R$_4$NH$_2$ in which R$_4$ is as defined in claim 1.

9. A pharmaceutical composition comprising at least one compound of formula (I) or a hydrate or a solvate thereof in combination with one or more pharmaceutically acceptable excipients:

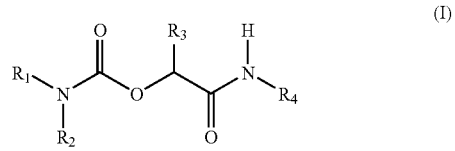

in which
R$^1$ represents a C$_{5-26}$-alkyl, C$_{5-26}$-alkenyl or C$_{5-26}$-alkynyl group or a polyunsaturated aliphatic carbon group comprising between 5 and 26 carbon atoms and comprising at least two unsaturations chosen from double and triple bonds;
R$_2$ represents a hydrogen atom or a C$_{1-6}$-alkyl group;
R$_3$ represents a hydrogen atom or a C$_{1-3}$-alkyl group; and
R$_4$ represents a hydrogen atom or a C$_{1-4}$-alkyl, C$_{3-7}$-cycloalkyl or C$_{3-7}$-cycloalkyl-C$_{1-3}$-alkyl group.

10. The composition according to claim 9, wherein:
R$_1$ represents a C$_{5-26}$-alkyl group, a C$_{5-26}$-alkenyl group or a polyunsaturated aliphatic carbon group comprising between 5 and 26 carbon atoms and comprising at least two unsaturations chosen from double bonds;
R$_2$ represents a hydrogen atom or a C$_{1-6}$-alkyl group;
R$_3$ represents a hydrogen atom or a C$_{1-3}$-alkyl group; and $R_4$ represents a hydrogen atom or a $C_{1-4}$-alkyl, $C_{3-7}$-cycloalkyl or $C_{3-7}$-cycloalkyl-$C_{1-3}$-alkyl group.

11. The composition according to claim 9, wherein:

$R_3$ represents a hydrogen atom or a $C_{1-3}$-alkyl group; and
$R_4$ represents a hydrogen atom or a $C_{1-4}$-alkyl group.

12. The composition according to claim 9, wherein:

$R_1$ represents a $C_{10-20}$-alkyl, $C_{10-20}$-alkenyl or $C_{10-20}$-alkynyl group or a polyunsaturated aliphatic carbon group comprising between 10 and 20 carbon atoms and comprising at least two unsaturations chosen from double and triple bonds;
$R_2$ represents a hydrogen atom or a $C_{1-6}$-alkyl group;
$R_3$ represents a hydrogen atom or a $C_{1-3}$-alkyl group; and
$R_4$ represents a hydrogen atom or a $C_{1-4}$-alkyl, $C_{3-7}$-cycloalkyl or $C_{3-7}$-cycloalkyl-$C_{1-3}$-alkyl group.

13. The composition according to claim 9, wherein:

$R_1$ represents a $C_{10-20}$-alkyl group, a $C_{10-20}$-alkenyl group or a polyunsaturated aliphatic carbon group comprising between 10 and 20 carbon atoms and comprising at least two unsaturations chosen from double bonds;
$R_2$ represents a hydrogen atom or a $C_{1-6}$-alkyl group;
$R_3$ represents a hydrogen atom or a $C_{1-3}$-alkyl group; and
$R_4$ represents a hydrogen atom or a $C_{1-4}$-alkyl group.

\* \* \* \* \*